(12) United States Patent
Fairweather et al.

(10) Patent No.: US 11,391,650 B2
(45) Date of Patent: Jul. 19, 2022

(54) METHOD AND APPARATUS FOR PERFORMING WATER SAMPLING WITH AN UNMANNED AERIAL VEHICLE

(71) Applicant: Fairweather IT LLC, Bozeman, MT (US)

(72) Inventors: Ian Stuart Fairweather, Bozeman, MT (US); James Patrick Jonas, Bozeman, MT (US)

(*) Notice: Subject to any disclaimer, the term of this patent is extended or adjusted under 35 U.S.C. 154(b) by 303 days.

(21) Appl. No.: 16/844,224

(22) Filed: Apr. 9, 2020

(65) Prior Publication Data

US 2020/0326262 A1 Oct. 15, 2020

Related U.S. Application Data

(60) Provisional application No. 62/832,123, filed on Apr. 10, 2019.

(51) Int. Cl.
| | | |
|---|---|---|
| *G01N 1/10* | (2006.01) | |
| *B64C 39/02* | (2006.01) | |
| *B64D 47/08* | (2006.01) | |
| *B64D 41/00* | (2006.01) | |
| *G01N 33/18* | (2006.01) | |

(52) U.S. Cl.
CPC ............ *G01N 1/10* (2013.01); *B64C 39/024* (2013.01); *B64D 41/00* (2013.01); *B64D 47/08* (2013.01); *G01N 33/18* (2013.01); *B64C 2201/027* (2013.01); *B64C 2201/12* (2013.01); *B64C 2201/146* (2013.01); *G01N 2001/1031* (2013.01)

(58) Field of Classification Search
CPC .. G01N 1/10; G01N 33/18; G01N 2001/1031; B64C 39/024; B64C 2201/027; B64C 2201/12; B64C 2201/146; B64D 41/00; B64D 47/08
See application file for complete search history.

(56) References Cited

U.S. PATENT DOCUMENTS

| | | | |
|---|---|---|---|
| 9,650,136 B1 * | 5/2017 | Haskin | B64D 1/12 |
| 10,877,477 B1 * | 12/2020 | Fox | B64D 47/08 |
| 2017/0328814 A1 * | 11/2017 | Castendyk | G01N 1/12 |
| 2018/0244509 A1 * | 8/2018 | Curran | B66D 1/485 |

FOREIGN PATENT DOCUMENTS

| | | | |
|---|---|---|---|
| CN | 105699125 A | * | 6/2016 |
| CN | 106525493 A | * | 3/2017 |
| CN | 108583878 A | * | 9/2018 |
| CN | 108594682 A | * | 9/2018 |

(Continued)

*Primary Examiner* — Peter D Nolan
*Assistant Examiner* — Kenneth M Dunne
(74) *Attorney, Agent, or Firm* — Eric Hanscom (57) ABSTRACT

A UAV capable of sampling a hazardous body of water and a method of using the same. An electronic controller of the attached apparatus receives a first instruction to lower a sampling device at a specified rate into the body of water. The sampling device is connected to the apparatus via a line, and the sampling device is lowered by unspooling the line from a reel. The sampling device is lowered at the specified rate into the body of water based on the instruction and is retrieved from the body of water. A line-cutting device can cut the line should the sampling device get caught up in an obstruction.

5 Claims, 5 Drawing Sheets

(56) References Cited

FOREIGN PATENT DOCUMENTS

| | | | | |
|---|---|---|---|---|
| CN | 108982159 A | * | 12/2018 | ............... G01N 1/10 |
| CN | 109060421 A | * | 12/2018 | |
| CN | 110465976 A | * | 11/2019 | |
| EP | 3112840 A1 | * | 1/2017 | ........... B64C 39/024 |
| WO | WO-2015076886 A2 | * | 5/2015 | ........... B64C 39/024 |

* cited by examiner

METHOD AND APPARATUS FOR PERFORMING WATER SAMPLING WITH AN UNMANNED AERIAL VEHICLE

CROSS-REFERENCE TO RELATED APPLICATIONS

This application claims priority back to U.S. Provisional No. 62/832,123, filed 10 Apr. 2019, the contents of which are incorporated by reference.

BACKGROUND

Water remediation is the field of measuring and removing pollutants or contaminants from ground water or surface bodies of water. In certain cases, a governmental authority can perform or request water remediation action to be taken in order to reduce negative effects upon human health and upon the natural environment. In addition to governmental authorities, other parties can perform environmental remediation services in order to help protect the environment. However, water sampling using human labor is expensive and potentially dangerous, as people can drown under some circumstances, and in other cases the water to be sampled is dangerously polluted to the point where is it unsafe for a human to come into contact with that body of way. A drone provides an effective way to remove humans from potentially hazardous conditions, and do the work that they would have done in a cost-efficient manner.

SUMMARY

Herein disclosed is a method and/or apparatus for performing water sampling using a drone or unmanned aerial vehicle (UAV). The apparatus of one or more embodiments can be an attachment that can be attached to the UAV. Once the attachment is attached to the UAV, the attachment can assist one or more users in collecting samples from or collecting data about a body of water. For example, the attachment can assist one or more users in collecting discrete water samples from the body of water.

With one or more embodiments, the attachment can be in the form an attachable plate, which can be configurable to attach to any type of multirotor UAV. With one or more embodiments, the attachment can allow the UAV to carry a payload capacity of 6 kg or greater. The attachable plate can be referred to herein as a water sampling platform (i.e., a "WaSP"). As described in more detail below, the apparatus of one or more embodiments can enable users in collecting water samples/information at depths that are not achievable by other approaches of sampling water.

While multiple embodiments are disclosed, still other embodiments will become apparent to those skilled in the art from the following detailed description. As will be apparent, certain embodiments, as disclosed herein, are capable of modifications in various aspects without departing from the spirit and scope of the claims as presented herein. Accordingly, the detailed description hereinbelow is to be regarded as illustrative in nature and not restrictive.

BRIEF DESCRIPTION OF THE DRAWINGS

The following figures illustrate embodiments of the subject matter disclosed herein. The claimed subject matter may be understood by reference to the following description taken in conjunction with the accompanying figures, in which:

DETAILED DESCRIPTION

Unless otherwise specified, any use of any form of the terms "connect," "engage," "couple," "attach," or any other term describing an interaction between elements is not meant to limit the interaction to direct interaction between the elements and may also include indirect interaction between the elements described. In the following discussion and in the claims, the terms "including" and "comprising" are used in an open-ended fashion, and thus should be interpreted to mean "including, but not limited to . . . ." The various characteristics mentioned above, as well as other features and characteristics described in more detail below, will be readily apparent to those skilled in the art with the aid of this disclosure upon reading the following detailed description of the embodiments, and by referring to the accompanying drawings.

Within the field of water remediation, certain professionals may need to know the chemical composition and/or properties of certain bodies of water. These professionals can include scientists, policy makers, landowners, and/or other responsible parties, for example. These professionals generally need water-quality information in order to understand the chemical and physical nature of these water bodies. However, these bodies of water can include hazardous chemicals, hazardous thermal characteristics, can exhibit other dangers to the professionals, and/or can be inaccessible to the professionals, for example. In particular, mining pits, hazardous waste dumps, tailings impoundments and volcanic lakes can contain water that is hazardous to human health.

One approach of performing water sampling (from a hazardous body of water) is to perform remote collection of the water sample. Concerns regarding human safety and legal restrictions (as instituted by the Occupational Safety and Health Administration (OSHA) and the Mine Safety and Health Administration (MSHA)) can restrict professionals from directly sampling hazardous water bodies. Remote collection is generally necessary because professionals are not allowed to launch boats directly onto the water due to the safety risks posed by the water. As an example of hazardous conditions, certain pits can contain acidic water (which have pH levels between 3 and 4) and/or can have high concentrations of metals, for example.

One conventional approach of performing remote collection is to use a remotely-controlled boat that can perform water sampling. However, this conventional approach is very slow and still requires a human operator to launch and retrieve the remote-controlled boat from the edge of the water. As such, the human operator is still put at risk by virtue of being on shore near the hazardous water. Additionally, the remote-controlled boat can be large in size, and the human operator may need a vehicle-towed trailer to transport the remote-controlled boat to the desired location, which increases the cost and inconvenience of using this approach.

With another conventional approach of performing remote collection, a system is configured to use a pump in order to pump a water sample up to an unmanned aerial vehicle (UAV) for performing sample collection. Another conventional approach configures an UAV to use a static line to connect the UAV to sample collection equipment. The UAV then raises and lowers the sample collection equipment using the UAV's change in altitude. However, these conventional approaches of using UAVs to perform remote collection can only sample the surface of the water. Specifically, when using the pump to pump the water sample, the pump cannot reach the lower depths of the body of water, and thus the pump cannot pump water samples from these lower depths.

With regard to using the static line to connect to the sample collection equipment, Federal Aviation Administration (FAA) regulations mandate that the UAV's altitude shall not exceed 400 feet high. As such, the maximum configurable length of the static line is thus less than 400 feet, where the UAV flies at its highest allowable altitude, and where connected the collection equipment is hovering near the ground. As such, when the UAV (of this conventional approach) collects water, the maximum depth that the UAV can collect water at is limited by the length of the static line. Specifically, the UAV can only collect water using the sample collection equipment at a maximum depth less than 400 feet, which corresponds to the maximum length of the static line.

Certain conventional approaches attempt to directly collect water samples by using boats to transport professionals upon the water bodies. However, such conventional approaches typically require at least two boats, where one boat collects the water samples, and the other boat acts as a rescue boat. Further, this conventional approach will generally require more people to be onsite and near any hazardous conditions. Further, these professionals generally must have specific training regarding water, thus increasing the cost of collecting the water samples.

In view of the above-described difficulties associated with the conventional approaches, one or more embodiments of the present invention allow users to remotely collect and sample water bodies without putting any humans in any direct risk of harm. One or more embodiments can also reduce the costs of sampling. Specifically, one or more embodiments can enable collection to be performed at a cheaper cost as compared to deploying a traditional boat-based sampling method. Further, one or more embodiments are directed to an unmanned technology for collecting water samples and for performing water-column profiles. Performing a water-column profile generally means determining the composition and/or characteristics of a given volume of water. As described in more detail below, with one or more embodiments of the present invention, a two-person team can safely collect a greater diversity of water samples and data, where the samples and data can be collected from different locations at different depths. In contrast to the conventional approaches, which are limited to collecting water at the surface (or water at a maximum depth of 400 feet), one or more embodiments are able to collect water at a deeper depth by using a level wind reel to raise and lower water sampling/monitoring equipment. One or more embodiments of the present invention can thus collect samples from depths greater than the aforementioned maximum flight altitude ceiling of 400 ft. Specifically, one or more embodiments has collected water at a depth of 446 ft during regular use.

One or more embodiments can also use calculated reel speeds to estimate a depth of a collected sample. As such, the UAV of one or more embodiments provides an excellent platform for collecting water samples at various depths at any location.

Figure 1:
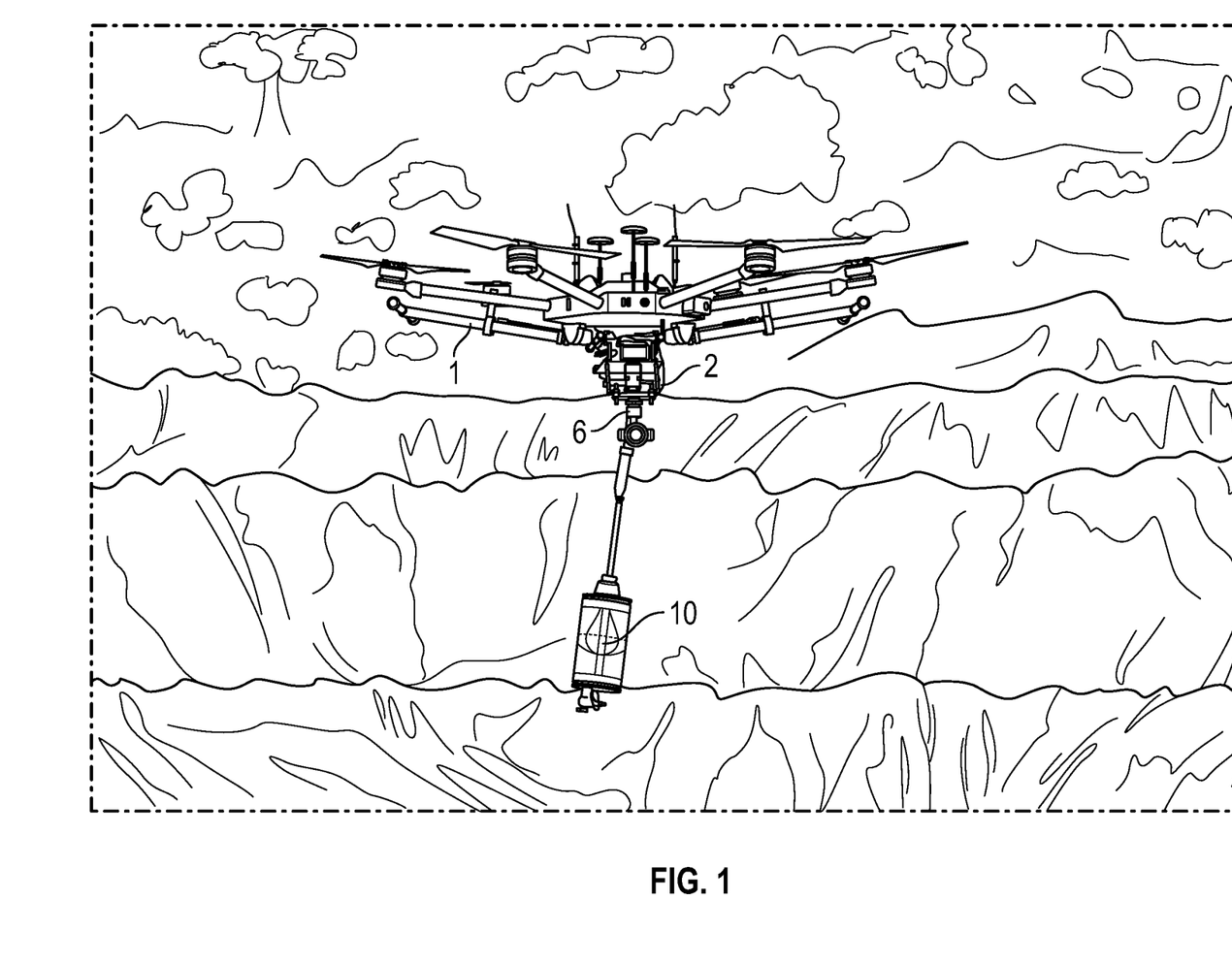
FIG. 1 is a side view of a UAV with the invention attached.

FIG. 1 is a forward facing view of a UAV with the invention attached. FIG. 1 illustrates an example apparatus 2 of one or more embodiments. One or more embodiments can be directed to an apparatus that can be attached to any unmanned aerial vehicle (UAV) 1. Thus, one or more embodiments can operate independent of the specific UAV platform. As described above, with one or more embodiments, apparatus 2 can be a plate that can be attached to any type of UAV (with a UAV payload greater than 6 kg, for example). This apparatus can be referred to as a Water Sampling Platform (WaSP).

As described in more detail below, one or more embodiments of the present invention can be configured with a remotely-controlled level-wind reel for line management. One or more embodiments can use a planetary gear motor with a linear encoder to drive the level-wind reel of one or more embodiments.

Upon receiving an instruction from an operator, an electronic controller of one or more embodiments can initiate raising/lowering of a payload of sampling equipment. An example embodiment can raise/lower any payload (such as sampling equipment) that is less than or equal to about 3 kg (6.6 lbs.). One or more embodiments can raise and lower the payload in order to sample water at depths greater than 400 ft. As described above, the conventional approaches that use UAVs can only sample water at a depth of, at most, 400 ft, which corresponds to the maximum altitude that is permitted in accordance with FAA rules.

Another shortcoming of using the conventional approach of using a static line to connect the UAV with the payload is that, during flight, the payload will dangle far beneath the UAV. During flight, the payload will swing beneath the UAV, which will cause a pendulum effect of the payload. This pendulum effect will cause users of this conventional approach to lose control of the UAV during flight. If control is lost or impeded during flight, the UAV can crash or fly to an undesirable location and in areas with trees and other physical barriers, the line can be caught up in an obstruction, losing both the UAV and the sample. In contrast to the conventional approaches, while the UAV of one or more embodiments is in flight, the UAV can raise the payload to the body/belly of the UAV. By raising the payload up to the body/belly of the UAV, the UAV is able to exhibit better flight characteristics, and the control over the UAV's flight is improved.

In particular, the control over the UAV's flight is especially improved when the UAV is being flown in windy conditions. In the prior art where the sampling capsule hangs at the end of a static line, the wind will blow the sampling capsule away from the plumb line below the UAV. This will result in the operator of the UAV having to either "pendulum" the sampling capsule back and forth over the target, and "drop" the UAV suddenly when the sampling capsule is directly over the target, or locate the UAV significantly upwind of the target, assuming that the wind will blow the sampling capsule downwind over the target.

One or more embodiments can perform speed control when raising or lowering the payload. Upon receiving an instruction, one or more embodiments can remotely control a modified off-the-shelf fishing reel to raise and lower equipment into the water. The line of the reel will unspool, thus allowing the equipment to be lowered into the water. This will allow one or more embodiments to lower equipment into the water at any location, while keeping all flight electronics away from the hazardous water. The reel of one or more embodiments will also allow for the payload to be transported close to center of gravity of the UAV, as described above.

By performing speed control when raising and lowering the payload, one or more embodiments can raise/lower the payload at a proper rate/speed for the payload. For example, in order to accurately collect data with certain water monitoring equipment (e.g., a sonde), the speed at which the water monitoring equipment travels through the water may need to be limited to a certain speed. For example, in order to ensure proper collection of measurements, the maximum speed at which a sonde can travel through the water can be 1 ft/second. In accordance with one embodiment, the system can operate in accordance with configurable speeds when raising or lowering the payload. Thus, different types of water monitoring equipment can be lowered into the water at speeds that do not inhibit proper collection of water/measurements.

One or more embodiments of the present system are configured to lower/raise the sampling/monitoring equipment at customizable speeds. These customizable speeds can be programmed in the controller of the system of one or more embodiments. One or more embodiments can be configured with a plurality of speeds to operate the reel to unspool the line, which causes the reel to lower or raise the payload. The reel can be operated at, for example, a 100% level, a 50% level, and/or a 30% level. One or more embodiments may use a fine tune dial as well to achieve precise speed control. The relationship between speed of descent and power level can be programmed into the controller such that an operator will be able to lower the payload at a desired speed, by operating the system a specified power level.

Figure 2:
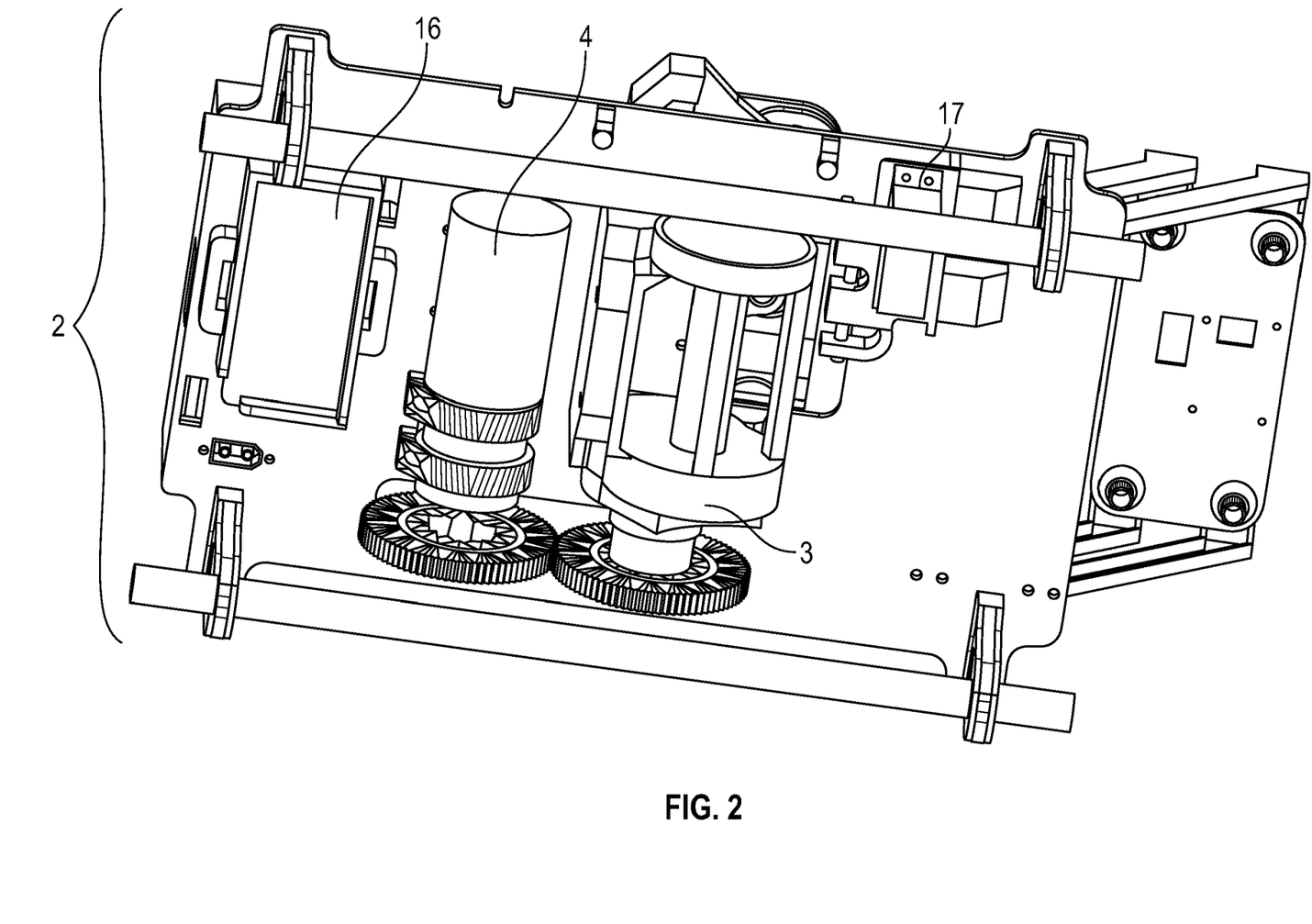
FIG. 2 is a top, perspective view of the invention.

FIG. 2 is a top, perspective view of the invention. FIG. 2 illustrates an example reel system 2 of one or more embodiments. One or more embodiments includes a level wind reel 3 that is geared to a direct-current (DC) motor 4. The motor 4 is a planetary gear motor with a linear encoder which allows the user to program specific speeds (such as ascent/descent rate of 1 m/s) and the motor with feedback from the encoder will move loads of different mass (1 kg vs 3 kg) at the set speeds. The level-wind reel 3 that is geared to the DC motor 4 provides a method to safely and to accurately lower and raise the water-quality monitoring equipment or water-collection sample bottles on braided lines. A battery tray 16 holds the battery and a messenger release. Certain payloads, such as a Niskin or Kemmerer water sample collection bottle require an external trigger to close, and thus capture a discrete sample at depth. The WaSP is outfitted with a remote-controlled servo release mechanism that releases a "messenger", typically a weight, that travels down the attachment line, and when it contacts the sample bottle, triggers the closure of the water bottle at depth. This embodiment allows a water sample to be collected at a specific depth. A FPV (first person view) camera gimbal 18 holds an FPV camera.

Figure 3:
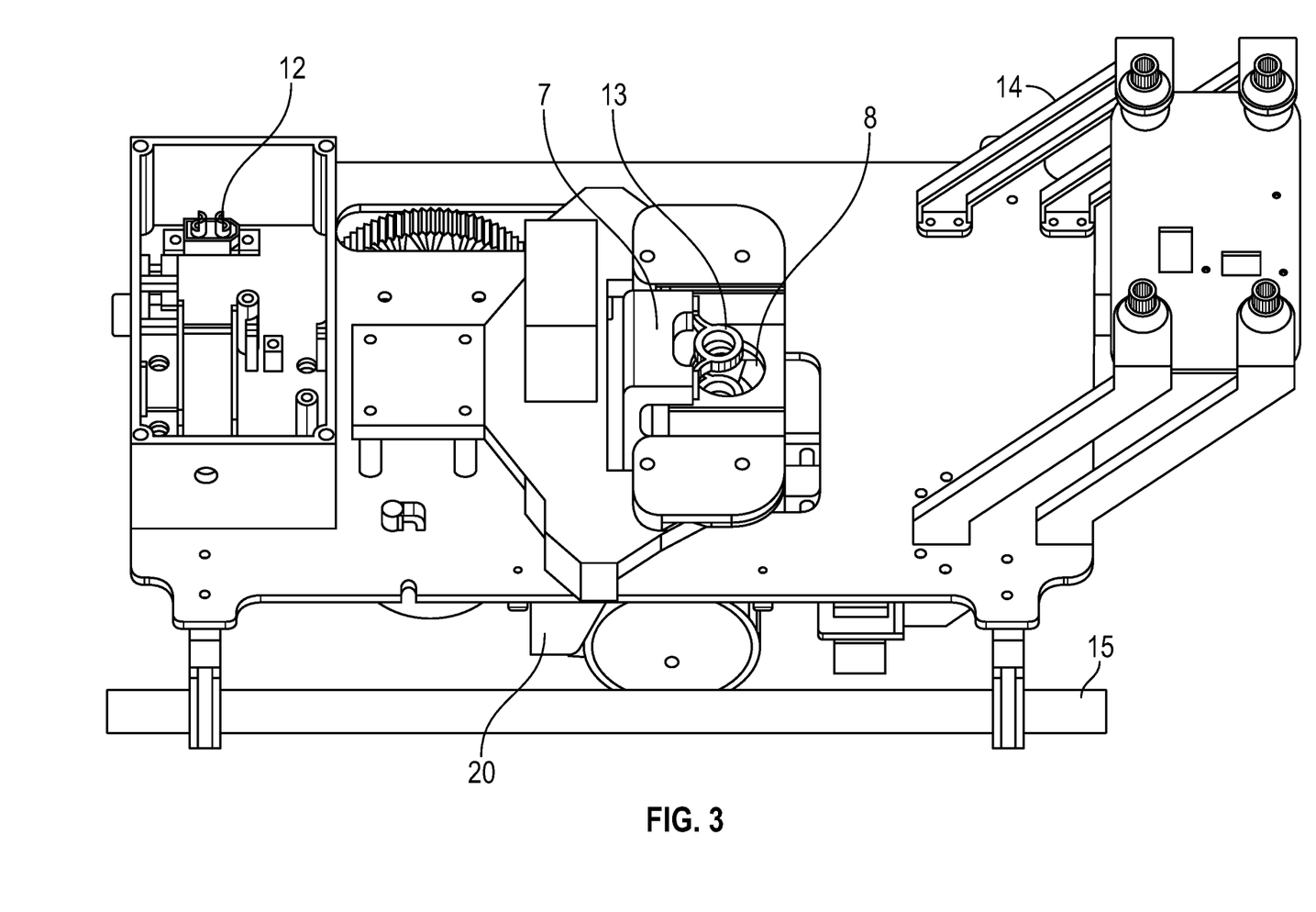
FIG. 3 is a bottom, perspective view of the invention.

FIG. 3 is a bottom, perspective view of the invention. FIG. 3 illustrates a lateral view of the example apparatus of one or more embodiments. As described in more detail below, apparatus 2 can include an electronic controller 5 for controlling the DC motor which controls movement of the aforementioned reel 3. A reel mounting bracket 20 secures the reel 3 to the WaSP plate 2. As described in more detail below, controller 5 can also control a line-cutting mechanism 7 (more fully described in FIGS. 3 and 4) that can cut the line that connects to the water sample, thus releasing the water sample, if necessary. The electronic controller is housed in a watertight controls housing 12.

Figure 4:
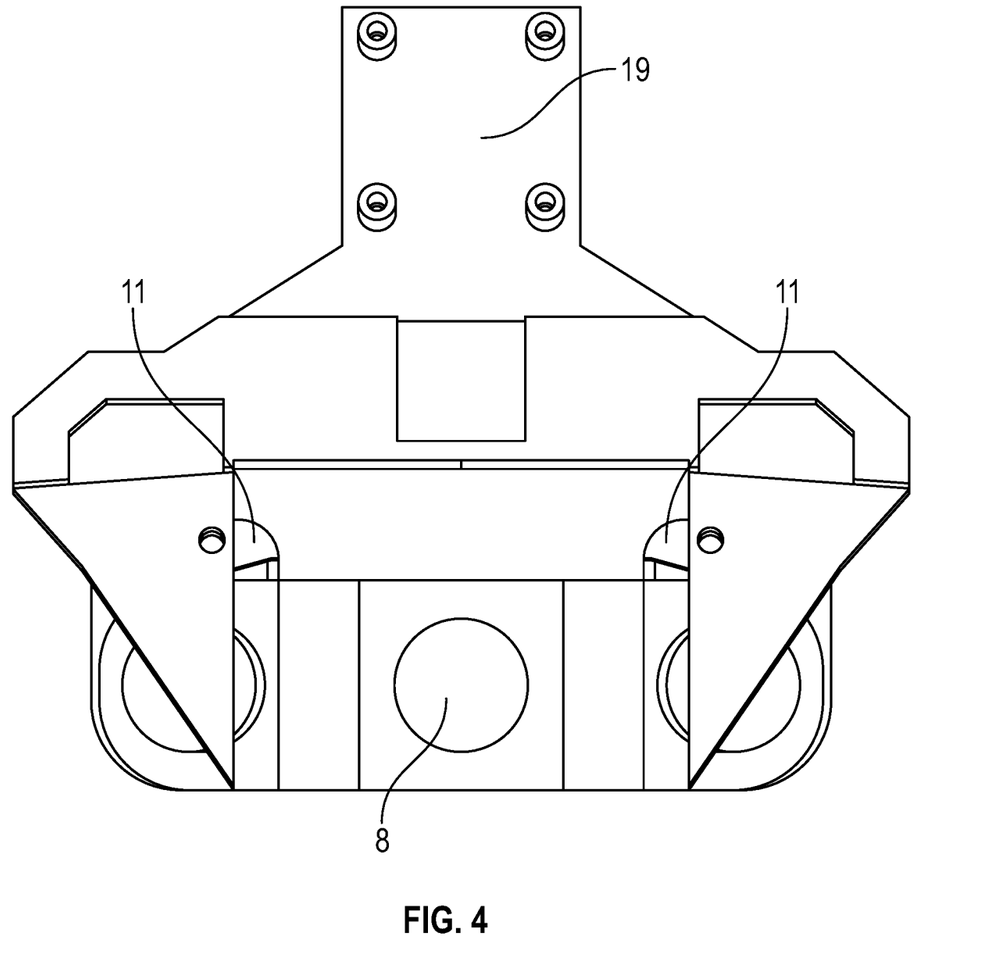
FIG. 4 is a front view of the line-cutting portion of the invention.
Figure 5:
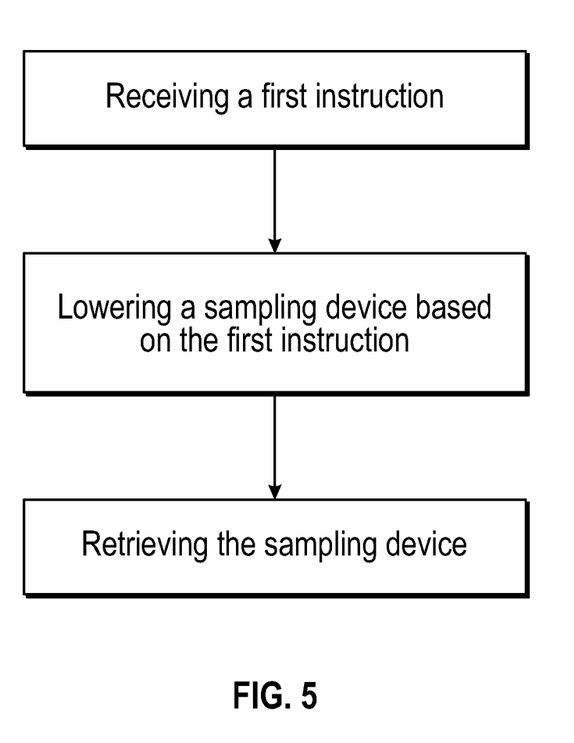
FIG. 5 contains a flowchart of an example method of one or more embodiments.

FIG. 4 is a front view of the line-cutting portion of the invention. FIG. 4 illustrates a bottom view of the example apparatus of one or more embodiments. From the bottom of apparatus, the line is threaded through a hole 8, in order to connect to the water sample. The sides of hole are guarded from the top and bottom with payload line guards 13 so that the line is not accidentally cut by contact with the edge of hole. The line-cutting mechanism 7 has two opposing shears that, when directed by the electronic controller 5, can cut the line 6. The line 6 exits the reel 3, and goes through the line-cutting hole 8 and payload line guards 13. A camera gimbal 14 provides a mount upon which a camera can be attached. The apparatus 2 can be attached to a UAV upon the UAV payload rails 15. Two cutter mounts 11 contain line-cutting shears. A servo-driven parallel gripper 19 forms the motion component to activate the line-cutting shears. A remote command is given to the servo, and the servo rotates, moving the parallel gripper arms, and thus closing the cutting shears. This motion can cut the line and release the payload in the event that the payload is stuck, or if the UAV needs to return to home for any reason or emergency FIG. 5 contains a flowchart of an example method of one or more embodiments. The method samples a hazardous body of water with an apparatus attached to an unmanned aerial vehicle. The method, includes receiving, by an electronic controller of the attached apparatus, an instruction to lower a sampling device at a specified rate into the body of water. The sampling device is connected to the apparatus via a line, and the sampling device is lowered by unspooling the line from a reel. The method also includes lowering the sampling device at the specified rate into the body of water based on the instruction. The method also includes retrieving the sampling device. What is claimed is:

In one preferred embodiment of the invention, we propose a method of obtaining a sample from a body of water, comprising four steps, including a first step, a second step, a third step, and a fourth step, where the first step is to acquire a UAV for water sampling, where the UAV comprises, a drone, a motor attachment, a line, and a sample capsule, where the motor attachment is removably connected to the drone, and where the line extends from the motor attachment to the sample capsule, and where the motor attachment comprises a linear encoder motor, a reel, a controller, and a line-cutting mechanism with a line-cutting hole, where the line is wound around reel, and the controller controls the linear encoder motor, where the second step is to have a pilot in command of the UAV send a first signal to the controller causing the linear encoder motor to unwind the line to allow the sample capsule to take a specimen from a body of water, where the third step is to have the pilot in command of the UAV send a second signal to the controller which causes the linear encoder motor to wind in the line, and where the fourth step is to have the pilot in commend of the UAV pilot the UAV to a desired location where the specimen can be removed from the UAV, where the first signal includes a first speed parameter, and the second signal includes a second speed parameter, where the first speed parameter represents a first fixed rate of unwinding, and the second speed parameter represents a second fixed rate of winding, where the first fixed rate of unwinding and the second fixed rate of winding are both fixed numbers that are not dependent upon a weight of the specimen, where the motor attachment comprises a DC motor, where the motor attachment comprises a motor gear with a plurality of motor gear teeth, and the reel comprises a reel gear with a plurality of reel gear teeth, where the plurality of motor gear teeth mesh with the plurality of reel gear teeth, such that as the motor gear rotates, it imparts a rotation to the reel gear, where the line passes from the reel, through the line-cutting hole in the line-cutting device, and then connects to the sample capsule, where the line-cutting device can be activated by the pilot-in-command to cut the line should the sample capsule become tangled, thereby allowing the UAV to be retrieved by the pilot in command, where the line-cutting mechanism comprises two opposing shears and a line-cutting motor with line cutting gears attached to the two opposing shears, where, when the pilot in command transmits a line-cutting order, the line-cutting motor engages the line-cutting gears to move in opposite directions, bringing a first cutting surface of a first shear into contact with a second cutting surface of a second shear, such that the line is cut.

In a related embodiment, the motor attachment additionally comprises a controls housing, where the controller is housed in the controls housing, where the controls housing is a watertight container, where the motor attachment additionally comprises payload line guards, where the payload line guards protect the line, and additionally comprising a camera gimbal and a plurality of clamps, where the plurality of claims attach the apparatus to the UAV.

In another preferred embodiment, A UAV device for water sampling is proposed, where the UAV comprises, a drone, a motor attachment, a line, and a sample capsule, where the motor attachment is removably connected to the drone, and where the line extends from the motor attachment to the sample capsule, and where the motor attachment comprises a linear encoder motor, a reel, a controller, and a line-cutting mechanism with a line-cutting hole, where the line is wound around reel, and the controller controls the linear encoder motor, where a pilot in command of the UAV sends a first signal to the controller causing the linear encoder motor to unwind the line to allow the sample capsule to take a specimen from a body of water, where the pilot in command of the UAV sends a second signal to the controller which causes the linear encoder motor to wind in the line, and where the pilot in commend of the UAV pilots the UAV to a desired location where the specimen can be removed from the UAV, where the first signal includes a first speed parameter, and the second signal includes a second speed parameter, where the first speed parameter represents a first fixed rate of unwinding, and the second speed parameter represents a second fixed rate of winding, where the first fixed rate of unwinding and the second fixed rate of winding are both fixed numbers that are not dependent upon a weight of the specimen, where the motor attachment comprises a DC motor, where the motor attachment comprises a motor gear with a plurality of motor gear teeth, and the reel comprises a reel gear with a plurality of reel gear teeth, where the plurality of motor gear teeth mesh with the plurality of reel gear teeth, such that as the motor gear rotates, it imparts a rotation to the reel gear, where the line passes from the reel, through the line-cutting hole in the line-cutting device, and then connects to the sample capsule, where the line-cutting device can be activated by the pilot-in-command to cut the line should the sample capsule become tangled, thereby allowing the UAV to be retrieved by the pilot in command, where the line-cutting mechanism comprises two opposing shears and a line-cutting motor with line cutting gears attached to the two opposing shears, where, when the pilot in command transmits a line-cutting order, the line-cutting motor engages the line-cutting gears to move in opposite directions, bringing a first cutting surface of a first shear into contact with a second cutting surface of a second shear, such that the line is cut, where the motor attachment additionally comprises a controls housing, where the controller is housed in the controls housing, where the controls housing is a watertight container, where the motor attachment additionally comprises payload line guards, where the payload line guards protect the line, and additionally comprising a camera gimbal and a plurality of clamps, and where the plurality of claims attach the apparatus to the UAV.

The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and such variations are considered within the scope and spirit of the present disclosure. Alternative embodiments that result from combining, integrating, and/or omitting features of the embodiment(s) are also within the scope of the disclosure. While compositions and methods are described in broader terms of "having", "comprising," "containing," or "including" various components or steps, the compositions and methods can also "consist essentially of" or "consist of" the various components and steps. Use of the term "optionally" with respect to any element of a claim means that the element is required, or alternatively, the element is not required, both alternatives being within the scope of the claim.

Numbers and ranges disclosed above may vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the elements that it introduces. If there is any conflict in the usages of a word or term in this specification and one or more patent or other documents, the definitions that are consistent with this specification should be adopted.

Numerous other modifications, equivalents, and alternatives, will become apparent to those skilled in the art once the above disclosure is fully appreciated. It is intended that the following claims be interpreted to embrace such modifications, equivalents, and alternatives where applicable. Accordingly, the scope of protection is not limited by the description set out above but is only limited by the claims which follow, that scope including equivalents of the subject matter of the claims.

REFERENCE NUMBERS USED

1. UAV
2. Motor Attachment Device
3. Reel
4. DC motor
5. Electronic Controller
6. Line
7. Line-cutting mechanism
8. Line-cutting hole
9. Padding 10. Sample capsule
11. Line-cutting shears
12. Controls Housing
13. Payload line guards
14. Camera gimbal
15. UAV Payload Rails
16. Battery tray
17. Messenger release
18. FPV camera gimbal
19. Servo-powered parallel gripper

What is claimed is:

1. A method of obtaining a sample from a body of water, consisting of four steps:
including a first step, a second step, a third step, and a fourth step,
where the first step is to acquire a UAV for water sampling, wherein the UAV comprises,
a drone, a motor attachment, a line, and a sample capsule,
wherein the motor attachment is removably connected to the drone, and wherein the line extends from the motor attachment to the sample capsule, and wherein the motor attachment comprises a linear encoder motor, a reel, a controller, and a line-cutting mechanism with a line-cutting hole, wherein the line is wound around reel, and the controller controls the linear encoder motor,
wherein the second step is to have a pilot in command of the UAV send a first signal to the controller causing the linear encoder motor to unwind the line to allow the sample capsule to take a specimen from a body of water,
wherein the third step is to have the pilot in command of the UAV send a second signal to the controller which causes the linear encoder motor to wind in the line,
and wherein the fourth step is to have the pilot in commend of the UAV pilot the UAV to a desired location where the specimen can be removed from the UAV,
wherein the first signal includes a first speed parameter, and the second signal includes a second speed parameter, wherein the first speed parameter represents a first fixed rate of unwinding, and the second speed parameter represents a second fixed rate of winding,
wherein the first fixed rate of unwinding and the second fixed rate of winding are both fixed numbers that are not dependent upon a weight of the specimen, wherein the motor attachment comprises a DC motor, wherein the motor attachment comprises a motor gear with a plurality of motor gear teeth, and the reel comprises a reel gear with a plurality of reel gear teeth,
wherein the plurality of motor gear teeth mesh with the plurality of reel gear teeth, such that as the motor gear rotates, it imparts a rotation to the reel gear, wherein the line passes from the reel, through the line-cutting hole in the line-cutting device, and then connects to the sample capsule,
wherein the line-cutting device can be activated by the pilot-in-command to cut the line should the sample capsule become tangled, thereby allowing the UAV to be retrieved by the pilot in command,
wherein the line-cutting mechanism comprises two opposing shears and a line-cutting motor with line cutting gears attached to the two opposing shears, wherein, when the pilot in command transmits a line-cutting order, the line-cutting motor engages the line-cutting gears to move in opposite directions, bringing a first cutting surface of a first shear into contact with a second cutting surface of a second shear, such that the line is cut.

2. The method of claim 1, wherein the motor attachment additionally comprises a controls housing, wherein the controller is housed in the controls housing, wherein the controls housing is a watertight container, where the motor attachment additionally comprises payload line guards, wherein the payload line guards protect the line, and additionally comprising a camera gimbal and a plurality of clamps, wherein the plurality of clamps attach the apparatus to the UAV.

3. A method of obtaining a sample from a body of water:
comprising a first step of acquiring a UAV for water sampling, wherein the UAV comprises, a drone, a motor attachment, a line, and a sample capsule, wherein the motor attachment is removably connected to the drone, and wherein the line extends from the motor attachment to the sample capsule, and wherein the motor attachment comprises a linear encoder motor, a reel, a controller, and a line-cutting mechanism with a line-cutting hole, wherein the line is wound around reel, and the controller controls the linear encoder motor,
a second step of having a pilot in command of the UAV send a first signal to the controller causing the linear encoder motor to unwind the line to allow the sample capsule to take a specimen from a body of water,
a third step of having the pilot in command of the UAV send a second signal to the controller which causes the linear encoder motor to wind in the line,
and a fourth step of having the pilot in commend of the UAV pilot the UAV to a desired location where the specimen can be removed from the UAV,
wherein the first signal includes a first speed parameter, and the second signal includes a second speed parameter, wherein the first speed parameter represents a first fixed rate of unwinding, and the second speed parameter represents a second fixed rate of winding, wherein the first fixed rate of unwinding and the second fixed rate of winding are both fixed numbers that are not dependent upon a weight of the specimen,
wherein the motor attachment comprises a DC motor,
wherein the motor attachment comprises a motor gear with a plurality of motor gear teeth, and the reel comprises a reel gear with a plurality of reel gear teeth, wherein the plurality of motor gear teeth mesh with the plurality of reel gear teeth, such that as the motor gear rotates, it imparts a rotation to the reel gear,
wherein the line passes from the reel, through the line-cutting hole in the line-cutting device, and then connects to the sample capsule, wherein the line-cutting device can be activated by the pilot-in-command to cut the line should the sample capsule become tangled, thereby allowing the UAV to be retrieved by the pilot in command,
wherein the line-cutting mechanism comprises two opposing shears and a line-cutting servo motor with line cutting gears attached to the two opposing shears, where, when the pilot in command transmits a line-cutting order, the line-cutting motor engages the line-cutting gears to move in opposite directions, bringing a first cutting surface of a first shear into contact with a second cutting surface of a second shear, such that the line is cut.

4. A UAV device for water sampling:

wherein the UAV comprises, a drone, a motor attachment, a line, and a sample capsule, wherein the motor attachment is removably connected to the drone, and wherein the line extends from the motor attachment to the sample capsule, and wherein the motor attachment comprises a linear encoder motor, a reel, a controller, and a line-cutting mechanism with a line-cutting hole, wherein the line is wound around reel, and the controller controls the linear encoder motor, wherein a pilot in command of the UAV sends a first signal to the controller causing the linear encoder motor to unwind the line to allow the sample capsule to take a specimen from a body of water, wherein the pilot in command of the UAV sends a second signal to the controller which causes the linear encoder motor to wind in the line, and wherein the pilot in commend of the UAV pilots the UAV to a desired location where the specimen can be removed from the UAV, wherein the first signal includes a first speed parameter, and the second signal includes a second speed parameter, wherein the first speed parameter represents a first fixed rate of unwinding, and the second speed parameter represents a second fixed rate of winding, wherein the first fixed rate of unwinding and the second fixed rate of winding are both fixed numbers that are not dependent upon a weight of the specimen, wherein the motor attachment comprises a DC motor, wherein the motor attachment comprises a motor gear with a plurality of motor gear teeth, and the reel comprises a reel gear with a plurality of reel gear teeth, wherein the plurality of motor gear teeth mesh with the plurality of reel gear teeth, such that as the motor gear rotates, it imparts a rotation to the reel gear, wherein the line passes from the reel, through the line-cutting hole in the line-cutting device, and then connects to the sample capsule, where the line-cutting device can be activated by the pilot-in-command to cut the line should the sample capsule become tangled, thereby allowing the UAV to be retrieved by the pilot in command, wherein the line-cutting mechanism comprises two opposing shears and a line-cutting motor with line cutting gears attached to the two opposing shears, where, when the pilot in command transmits a line-cutting order, the line-cutting motor engages the line-cutting gears to move in opposite directions, bringing a first cutting surface of a first shear into contact with a second cutting surface of a second shear, such that the line is cut.

5. The UAV of claim 4, wherein the motor attachment additionally comprises a controls housing, where the controller is housed in the controls housing, wherein the controls housing is a watertight container, wherein the motor attachment additionally comprises payload line guards, wherein the payload line guards protect the line, and additionally comprising a camera gimbal and a plurality of clamps, where the plurality of clamps attach the apparatus to the UAV.

* * * * *